United States Patent
Keen et al.

(10) Patent No.: US 10,209,231 B2
(45) Date of Patent: Feb. 19, 2019

(54) ENHANCED CHEMICAL DETECTION USING ACID CATALYZED HYDROLYSIS

(71) Applicant: FLIR Detection, Inc., Stillwater, OK (US)

(72) Inventors: Steven Keen, Stillwater, OK (US); Lara Wald, Stillwater, OK (US); Mark Fisher, Stillwater, CA (US)

(73) Assignee: FLIR Detection, Inc., Stillwater, OK (US)

( * ) Notice: Subject to any disclaimer, the term of this patent is extended or adjusted under 35 U.S.C. 154(b) by 141 days.

(21) Appl. No.: 15/256,443

(22) Filed: Sep. 2, 2016

(65) Prior Publication Data

US 2018/0067088 A1    Mar. 8, 2018

(51) Int. Cl.
G01N 31/22 (2006.01)
G01N 31/10 (2006.01)
G01N 33/00 (2006.01)

(52) U.S. Cl.
CPC ........... G01N 31/227 (2013.01); G01N 31/10 (2013.01); G01N 33/0057 (2013.01)

(58) Field of Classification Search
None
See application file for complete search history.

(56) References Cited

U.S. PATENT DOCUMENTS

| | | |
|---|---|---|
| 4,788,039 A | 11/1988 | Glattstein |
| 6,558,526 B2 | 5/2003 | Aker et al. |
| 7,208,122 B2 | 4/2007 | Swager et al. |
| 7,393,503 B2 | 7/2008 | Swager et al. |
| 7,419,636 B2 | 9/2008 | Aker et al. |
| 7,662,309 B2 | 2/2010 | Swager et al. |
| 7,799,573 B2 | 9/2010 | Deans et al. |
| 7,943,062 B2 | 5/2011 | Swager et al. |
| 8,323,576 B2 | 12/2012 | Aker et al. |
| 8,377,713 B2 | 2/2013 | Miller et al. |
| 8,465,678 B2 | 6/2013 | Swager et al. |
| 8,647,579 B2 | 2/2014 | La Grone et al. |
| 9,005,524 B2 | 4/2015 | Deans et al. |
| 9,068,960 B2 | 6/2015 | Wald et al. |
| 2012/0003746 A1 | 1/2012 | Amisar |

(Continued)

FOREIGN PATENT DOCUMENTS

CN    103502817    1/2014

OTHER PUBLICATIONS

Chambers, D.M. Perspectives on Pentaerythritol Tetranitrate (PETN) Decomposition, 2002, Lawrence Livermore National Laboratory, retrieved from internet site https://e-reports-ext.llnl.gov/pdf/244673.pdf.*

*Primary Examiner* — Xiaoyun R Xu
(74) *Attorney, Agent, or Firm* — Haynes and Boone, LLP (57) ABSTRACT

Various techniques are provided to determine the presence of trace chemicals corresponding to various materials of interest. In one example, a method includes receiving a vapor-phase nitric acid precursor. The vapor-phase nitric acid precursor is subsequently hydrolyzed in the presence of an acid catalyst to form nitric acid. The nitric acid is then received at a chemical reporter of a chemical detector. A response of the chemical reporter to the nitric acid is detected by the chemical reporter to determine whether materials of interest are present. Additional methods and related devices are also provided.

20 Claims, 8 Drawing Sheets

(56) References Cited

U.S. PATENT DOCUMENTS

| | | |
|---|---|---|
| 2014/0017803 A1 | 1/2014 | Deans et al. |
| 2015/0285780 A1 | 10/2015 | Kelley et al. |
| 2015/0330957 A1 | 11/2015 | Wald et al. |
| 2016/0084772 A1 | 3/2016 | Nayak et al. |

* cited by examiner

ENHANCED CHEMICAL DETECTION USING ACID CATALYZED HYDROLYSIS

TECHNICAL FIELD

The present invention relates generally to chemical detection and, more particularly, to the detection of trace materials of interest.

BACKGROUND

Detection of explosives for security is an area of ongoing global concern. Concerted efforts have been focused on the detection of trace amounts of explosives, including nitrogen-based explosives.

Conventional detection methods, such as X-ray diffraction, nuclear quadruple resonance, ion mobility spectrometry, mass spectrometry, and gas chromatography are known and are highly sensitive and effective. Systems used to carry out these methods, however, are expensive, difficult to maintain, susceptible to false positives, and are not easily manufactured into low-power, portable devices.

Colorimetric techniques are known that can detect the presence of nitrogen-based explosives. Portable colorimetric chemical kits have the value of displaying interpreted optical signals with fast response times. These methods, however, have a number of disadvantages, including low sensitivity, high false alarm rates, and inconvenient analysis and clean-up procedures due to the liquid-based detection mechanisms. In addition, these methods can often expose users to large quantities of chemicals through repeated wet-chemistry style sampling steps.

SUMMARY

In various embodiments, a non-volatile acid catalyst (e.g., also referred to as a reactant or acidic reagent) is provided that facilitates the detection of certain nitrogen-based explosives at a chemical reporter upon hydrolysis of the nitrogen-based explosives. Hydrolysis of the nitrogen-based explosives yields nitric acid, which causes the chemical reporter to provide a detectable response. Nitrogen-based explosives may cause other chemical reporters to provide detectable responses, and additional materials of interest, such as peroxide-based explosives, may also cause chemical reporters to provide detectable responses.

Accordingly, various techniques are provided for the detection of trace amounts of nitrogen-based explosives without the disadvantages of the prior art. Such techniques are particularly useful in the detection of nitrate esters, such as nitroglycerin, and nitramines, such as Research Department Explosive (RDX). In some embodiments, the presence of a nitrogen-based explosive is based on the detection of a response of a reporter to the hydrolysis product of the nitrogen-based explosive.

In one embodiment, a method includes receiving a vapor-phase nitric acid precursor; hydrolyzing the vapor-phase nitric acid precursor in the presence of an acid catalyst to form nitric acid; receiving the nitric acid at a chemical reporter of a chemical detector; and detecting, by the chemical detector, a response of the chemical reporter to the nitric acid to determine whether materials of interest are present.

In another embodiment, a device includes an inlet configured to receive a vapor-phase nitric acid precursor; an acid catalyst configured to react with the vapor-phase nitric acid precursor to form nitric acid; and a chemical detector comprising a chemical reporter configured to respond to the nitric acid, wherein the chemical reporter is configured to detect a response of the chemical reporter to the nitric acid to determine whether materials of interest are present.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

In accordance with various embodiments disclosed herein, a non-volatile acid catalyst (e.g., also referred to as a reactant or acidic reagent) is provided that enhances the detection of one or more materials of interest. In some embodiments, the acid catalyst reacts with a nitrogen-based explosive to increase the rate of hydrolysis of the nitrogen-based explosive, thereby increasing the rate of production of nitric acid. A chemical reporter then receives the nitric acid and responds to the nitric acid to produce a detectable result. In various embodiments, a different chemical reporter responds to the nitrogen-based explosive to produce a detectable result. Advantageously, in some embodiments, the nitrogen-based explosive is detectable at two different chemical reporters based on two different detection techniques. In yet other embodiments, the acid catalyst reacts with other materials of interest (e.g., peroxide-based explosives) to provide results that signal the presence of other materials of interest.

Devices and related methods are provided in accordance with a variety of techniques to detect the presence of trace chemicals corresponding to materials of interest using acid catalyzed hydrolysis. In this regard, certain materials of interest may exhibit a fluorescent response, a change in fluorescence, a luminescent response, a change in luminescence, an infrared/Raman response, or a change in resistivity when exposed to an acid catalyst.

Various nitrogen-based explosives, including nitrate esters and nitramines, undergo acid catalyzed hydrolysis to produce nitric acid. For example, when an acid catalyst reacts with nitroglycerin, one of the products of the reaction is nitric acid. The source of water in the reaction can be from water in the air or from water on the surface of the acid catalyst.

The produced nitric acid is received by a chemical reporter in a chemical detector. The chemical reporter responds to the nitric acid to provide a detectable response. In some embodiments, this response may be the result of a change in the chemical reporter that may be detected at a particular type of detector of the chemical reporter, which signals the presence of a material of interest (e.g., a nitrogen-based explosive). For example, in some embodiments, the change may be a change in fluorescence of the chemical reporter that is detected by an optical detector. In some embodiments, the change may be a change in resistivity of the chemical reporter that is detected by an appropriate electrical detector. In some embodiments, the change may be an infrared/Raman response that is detected by an appropriate infrared/Raman response detector. In this way, materials of interest are identified in a convenient, low cost, rapid, and highly portable manner.

Advantageously, the chemical reporter is operable to detect any nitrogen-based explosive that produces nitric acid after hydrolysis. Thus, rather than being specific to a single explosive, the chemical reporter is able to detect a wide variety of nitrogen-based explosives, including, but not limited to, pentaerythritol tetranitrate (PETN), ethylene glycol dinitrate (EGDN), nitroglycerin, nitroglycerin containing powders such as double-based and triple-based smokeless powders, and cyclotrimethylenetrinitramine (RDX). Additional materials of interest (e.g., peroxide-based explosives) are also detectable as further discussed herein.

In accordance with various embodiments further discussed herein, a change in the chemical reporter may be combined with additional chemical detection techniques to confirm the presence of a nitrogen-based explosive. For example, in some embodiments, an additional chemical reporter that responds to the nitrogen-based explosive (rather than to nitric acid) may be present in the chemical detector. If a change in the additional chemical reporter is detected at a detector, this signals the presence of the nitrogen-based explosive.

In some embodiments, such detection techniques may be combined with additional chemical detection techniques to provide methods and systems for detecting additional classes of materials. For example, certain peroxide-based explosives, such as triacetone triperoxide (TATP) may be detected using, for example, luminescent methods.

Figure 1:
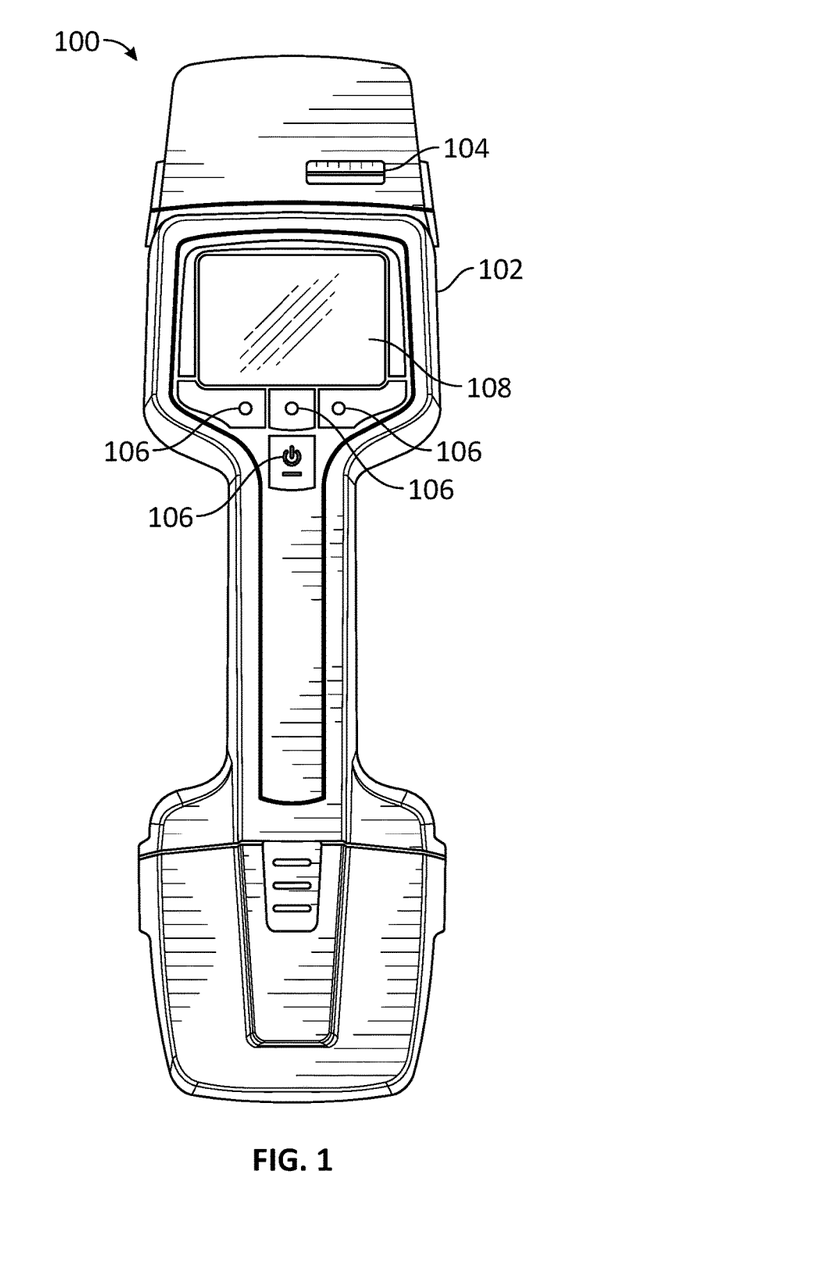
FIG. 1 illustrates an external view of a trace material detection device in accordance with an embodiment of the disclosure.

Turning now to the drawings, FIG. 1 illustrates an external view of a trace material detection device 100 in accordance with an embodiment of the disclosure. For example, in some embodiments, device 100 may be implemented as a handheld portable detector capable of detecting explosives and/or other materials.

As shown, device 100 includes a housing 102, a slot 104, user controls 106, and a display 108. In various embodiments, additional components of device 100 (e.g., further illustrated in FIG. 2) may be distributed at physical locations internal to and/or external to housing 102.

In operation, sampling media may be brought into physical contact with one or more surfaces to be tested. For example, in some embodiments, a user may wipe the media (e.g., also referred to as a "sampling swab") against a surface of interest to collect trace amounts of one or more test substances resident on the surface. The user then inserts the media into slot 104 after which additional operations and analysis are performed as further discussed herein. In some embodiments, the media may be implemented using an appropriate substrate such as polytetrafluoroethylene (PTFE), an aramid polymer, polyethylene, polyester, paper, and/or other materials.

In some embodiments, use of the media may not be necessary, as an inlet may be used to directly sample ambient air for vapor-phase analytes. Additional devices may be used to direct the analytes into the inlet, such as an air filter/concentrator positioned in the flow path of the analytes.

User controls 106 receive user input to operate device 100. As shown in FIG. 1, user controls 106 may be implemented as physical buttons. In other embodiments, user controls 106 may be implemented by one or more keyboards, levers, joysticks, touchscreens, and/or other controls. In some embodiments, user controls 150 may be integrated with display 108 as a touchscreen.

Display 108 presents information to the user of device 100. For example, FIG. 1 illustrates a warning message provided on display 108 in response to a detected material. In various embodiments, display may be implemented as a liquid crystal display (LCD), an organic light emitting diode (OLED) display, and/or any other appropriate display.

Figure 2:
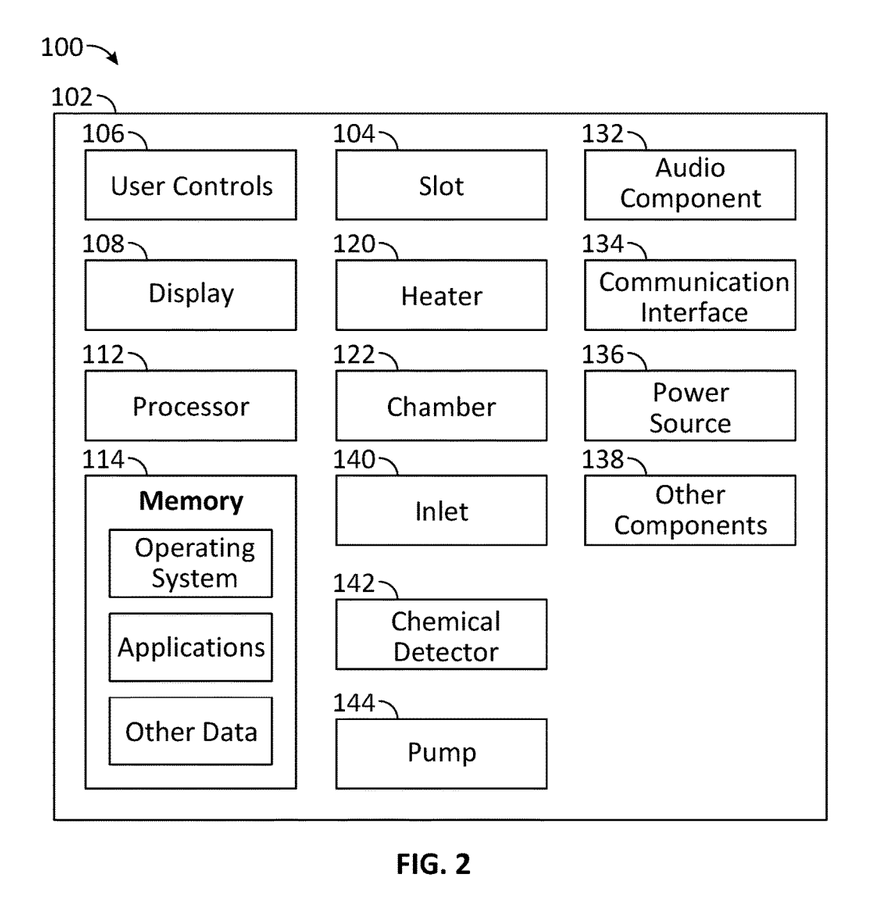
FIG. 2 illustrates a block diagram of a trace material detection device in accordance with an embodiment of the disclosure.

Additional features of device 100 are further illustrated in FIG. 2. FIG. 2 illustrates a block diagram of device 100 in accordance with an embodiment of the disclosure. In addition to several previously discussed components shown in FIG. 1, FIG. 2 further illustrates a processor 112, a memory 114, a heater 120, a chamber 122, an audio component 132, a communication interface 134, a power source 136, an inlet 140, a chemical detector 142, a pump 144, and other components 138.

Processor 112 may be implemented as one or more microprocessors, microcontrollers, system on a chip (SoC), application specific integrated circuits (ASICs), programmable logic devices (PLDs) (e.g., field programmable gate arrays (FPGAs), complex programmable logic devices (CPLDs), field programmable systems on a chip (FPSCs), or other types of programmable devices), or other processing devices used to control the operations of device 100. In this regard, processor 112 may execute machine readable instructions (e.g., software, firmware, or other instructions) stored in memory 114.

Memory 114 may be implemented as a machine readable medium storing various machine readable instructions and data. For example, in some embodiments, memory 114 may store an operating system 115 and one or more applications 116 as machine readable instructions that may be read and executed by processor 112 to perform various operations described herein. Memory 114 may also store various types of data 117 including, for example, chemical profiles, test sample identification results, and/or other information used or provided by the various components of device 100. In various embodiments, memory 114 may be implemented to store such instructions and data in a non-transitory manner and/or may be implemented with both transitory and non-transitory portions to selectively store all or portions of such instructions and data in either manner as appropriate.

Heater 120 may be implemented as one or more heaters (e.g., heaters 120A, 120B, and 120C further discussed herein) used to heat test samples (e.g., provided on a sampling swab) to a desired temperature such that the test samples at least partially vaporize to provide analytes for chemical detection. In some embodiments, heater 120 may be a resistive heater configured to heat the test samples, however other configurations may be used in other embodiments.

Chamber 122 provides a recessed volume within housing 102 and receives the media inserted through slot 104. While disposed in chamber 122, the media may be heated by heater 120.

Audio component 132 may be implemented, for example, as a speaker or other transducer with corresponding driver circuitry to provide audible sounds to a user of device 100. For example, in some embodiments, audio component 132 may provide audible signals in response to manipulation of user controls 106 and/or in response to the operations of processor 112 (e.g., to indicate that a particular material is present or is not present).

Communication interface 134 may be implemented as a wired and/or wireless interface connect device 100 (e.g., by Universal Serial Bus (USB), Ethernet, WiFi, Bluetooth, cellular, infrared, radio, and/or other protocols) with various external devices to update operating system 115, update applications 116, and/or communicate data 117. In some embodiments, communication interface 134 may connect to external power sources (e.g., a power outlet) to charge a battery of power source 136 and/or to directly power device 100.

Power source 136 may be implemented, for example, as a battery to permit mobile and remote use of device 100, a solar power source, a fuel cell, or wall power. In some embodiments, power source 136 may be a removable battery. Other components 138 may also be provided as appropriate for various types of devices 100 to support, for example, application specific operations of such devices.

Inlet 140, chemical detector 142, and pump 144 (e.g., implemented as an emission-based detector and/or using other technologies) may be used with heater 120 to provide a swab-based thermal desorber to perform vapor-based material detection as further discussed herein. In some embodiments, inlet 140 can directly sample ambient air for vapor-phase analytes without the need for the swab-based thermal desorber. For example, air from the ambient environment may be directly drawn into inlet 140.

Figure 3:
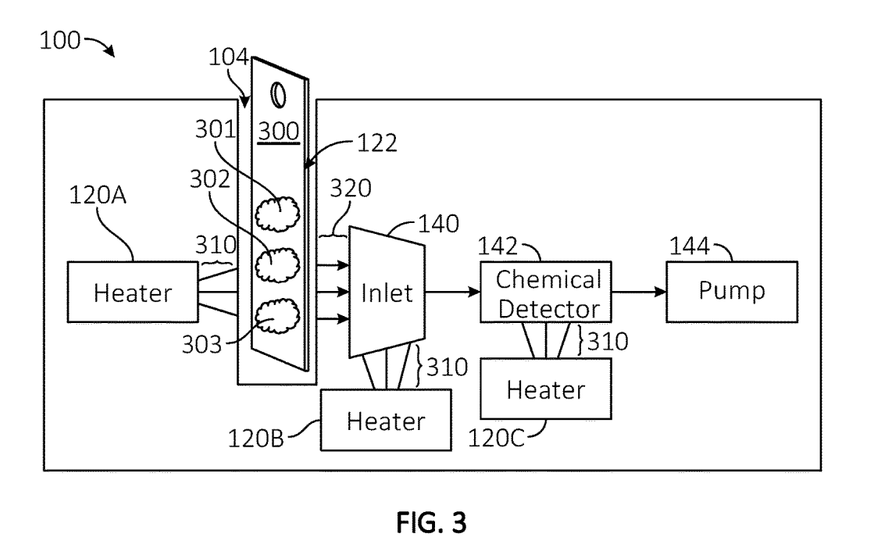
FIG. 3 illustrates an operational flow of analytes through a trace material detection device in accordance with an embodiment of the disclosure.

FIG. 3 illustrates an operational flow of analytes through device 100 in accordance with an embodiment of the disclosure. As shown, media 300 has been inserted through slot 104 in housing 102 and is positioned in chamber 122. Media 300 includes test samples 301, 302, and 303 which correspond to three different materials under test that have been picked up by the user's application of media 300 against one or more surfaces of interest.

As shown, heater 120 is implemented in multiple portions 120A, 120B, and 120C. Heater 120 operates (e.g., in response to control signals provided by processor 112) to apply heat 310 to media 300 and samples 301, 302, and 303 to raise their temperatures to a desired desorption temperature. In some embodiments, the detection temperature may be in the range of approximately 90 degrees C. to approximately 160 degrees C., however higher or lower temperatures may be used as desired.

In some embodiments, heaters 120A and 120B may be implemented to contact media 300. For example, heaters 120A and 120B may be mechanically moved to place the heaters 120A and 120B in contact with or in close proximity to media 300.

In FIG. 3, test sample 301 is 2,4,6-trinitrotoluene (TNT), test sample 302 is nitroglycerin, and test sample 303 is TATP, all of which may be detected by appropriate portions of chemical detector 144.

In this regard, test samples 301, 302, and 303 may be materials that partially or completely vaporize in response to heat 310 applied by heater 120 to provide analytes 320 (e.g., corresponding to vaporized portions of test samples 301, 302, and 303). The vaporized materials may exhibit various vapor pressures that facilitate the ability of pump 144 and chemical detector 142 to appropriately receive the analytes 320 (e.g., RDX has a vapor pressure of $5 \times 10^{-7}$ Torr at 20 degrees C., TNT has a vapor pressure of $2 \times 10^{-5}$ Torr at 20 degrees C., glycerol has a vapor pressure of $2.5 \times 10^{-3}$ Torr at 50 degrees C., and ethanol has a vapor pressure of 45 Torr at 20 degrees C.). Pump 144 operates to draw analytes 320 in and through inlet 140 into chemical detector 142. Based on interactions between analytes 320 and chemical detector 142 (e.g., performing trace detection), the presence of certain materials of interest may be determined.

Figure 4:
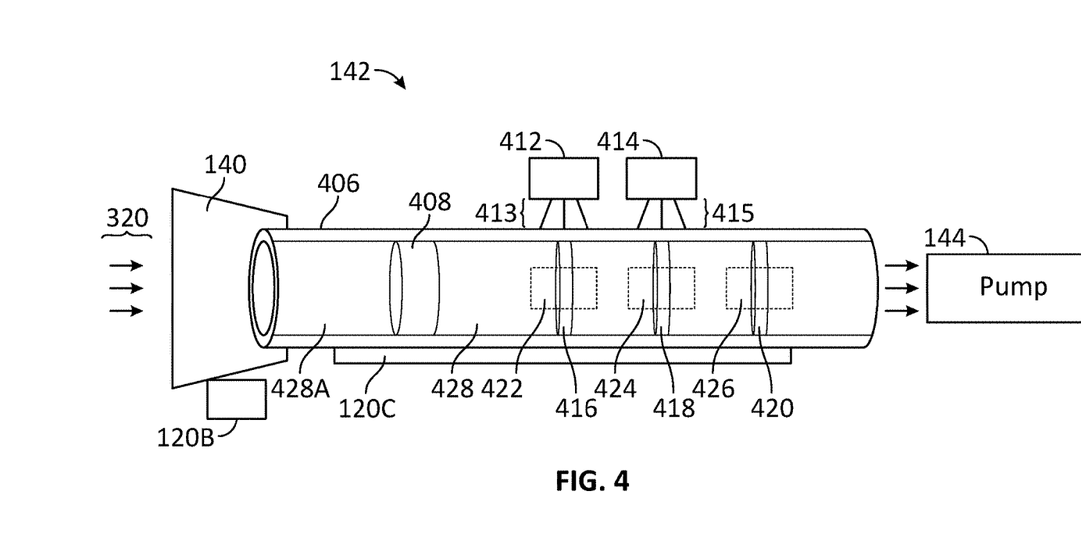
FIG. 4 illustrates a partial cross section view of a chemical detector of a trace material detection device in accordance with an embodiment of the disclosure.
Figure 5:
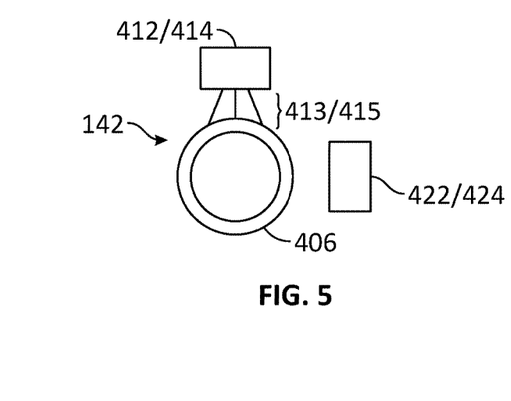
FIG. 5 illustrates a front view of a chemical detector of a trace material detection device.

FIGS. 4 and 5 illustrate various views of chemical detector 142 of device 100 in accordance with embodiments of the disclosure. As shown, the detector 142 includes an inlet 140, a tip heater 120B, a substrate reporter surface 406 (e.g., implemented as a capillary tube providing a flow path in these particular illustrated embodiments), a sensing channel 428 (e.g., implemented as a cavity within a capillary tube in these particular illustrated embodiments), an acid catalyst 408, a reporter heater 120C, various chemical reporters 416, 418, and 420, illumination sources 412 and 414 (e.g., also referred to as excitation sources) associated with chemical reporters 416 and 418, and response detectors 422, 424, and 426 associated with chemical reporters 416, 418, and 420.

Illumination sources 412 and 414 are optional, in that they are not required in chemical detection techniques that do not involve illumination of chemical reporters 416 and 418. For example, when a chemical reporter responds to a material of interest by exhibiting a change in resistivity, illumination sources 412 and 414 are not needed. In this case, the response of the chemical reporter is exhibited by a corresponding change in current or voltage that is detected by an appropriate detector. Thus, detection techniques other than those that involve excitation (e.g., radiation or light) are contemplated

As shown, when implemented as a capillary tube, substrate reporter surface 406 defines sensing channel 428, which provides a flow path through which vapor-phase analytes 320 pass through and react with acid catalyst 408 and interact with chemical reporters 416, 418, and 420.

Analytes 320 pass through inlet 140, where analytes 320 may be heated by tip heater 120B. Tip heater 120B maintains inlet 140 at a temperature sufficient to keep analytes 320 in the vapor-phase. More specifically, tip heater 120B prevents loss of analytes 320 while traveling through inlet 140 toward chemical reporters 416, 418, and 420. Pump 144 continues to pull the air with analyte(s) 320 in through inlet 140 and provides the ability to move vapor-phase analytes 320 from inlet 140 to sensing channel 428 and over acid catalyst 408 and chemical detectors 416, 418, and 420. Reporter heater 120C heats the interior surface of substrate reporter surface 406 to reduce the formation of "cold spots" where analytes 320 can lump together. In addition, reporter heater 120C helps analytes 320 desorb from chemical reporters 416, 418, and 420 to improve subsequent detection of analytes. In some embodiments, sensing channel 428 includes an initial portion 428A to prevent overheating of chemical reporters 416, 418, and 420 due to their proximity to tip heater 120B.

Once analytes 320 are introduced into sensing channel 428 beyond the initial portion 428A, acid catalyst 408 reacts with analytes 320. As shown, acid catalyst 408 is in the form of a coating on substrate reporter surface 406. For example, an aqueous or alcoholic suspension of acid catalyst 408 may be spin-coated on the interior of a capillary tube in liquid form and then dried. In this example, acid catalyst 408 may be spun out the front of the sensing channel 428, thereby coating the entire first portion of the capillary tube or trimmed to make a band.

Figure 6:
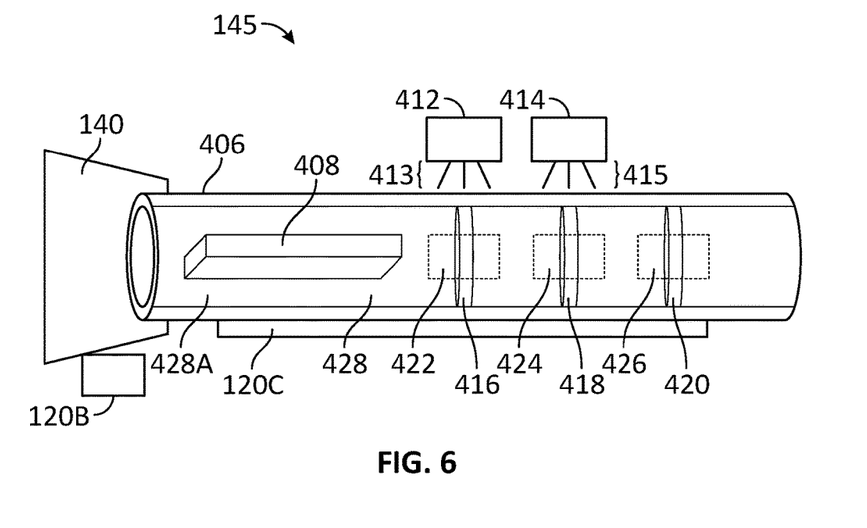
FIG. 6 illustrates a partial cross sectional view of a chemical detector of a trace material detection device in accordance with another embodiment of the disclosure.

FIG. 6 illustrates another chemical detector 145 in which acid catalyst 408 is in the form of a strip inserted into substrate reporter surface 406 (also implemented as a capillary tube), but is generally identical to chemical detector 142 of FIG. 4 in all other respects. Accordingly, the discussion of chemical detector 142 herein is also applicable to chemical detebtor 145.

In various embodiments, acid catalyst 408 includes one or more perfluorinated polymers containing sulfonic acid groups. For example, acid catalyst 408 may include a sulfonated tetrafluoroethylene based fluoropolymer-copolymer, such as Nafion® acid catalyst.

Nafion® acid catalyst

In other examples, acid catalyst 408 includes a copolymer of tetrafluoroethylene and a sulfonyl fluoride vinyl ether, such as Aquivion® acid catalyst.

Aquivion® acid catalyst

Other compounds including strongly acidic side groups attached to a chained backbone with low vapor pressure can be used. For example, a macro-porous polystyrene based ion exchange resin like Amberlyst® catalyst may be used as acid catalyst 408. Another example of a suitable acid catalyst 408 is polystyrene sulfonic acid.

In some embodiments, acid catalyst 408 includes one or more acids selected from the group consisting of sulfuric acid, hydrochloric acid, hydrofluoric acid, hydroiodic acid, hydrobromic acid, nitric acid, oxalic acid, hydrogen sulfate, phosphoric acid, formic acid, benzoic acid, acetic acid, propionic acid, or other organic acids of the form R—COOH where R is an alkyl, substituted alkyl, aryl, or substituted aryl group or at least one other cation donor.

Acid catalyst 408 ideally hydrolyzes the nitric acid precursors into nitric acid and provides no contribution to molecules in the vapor phase. In some embodiments, this can be accomplished by using an acid having a counter ion (negatively charged component that remains after a proton is donated) that has a sufficiently low vapor pressure at the operating temperature of chemical detector 142.

In various embodiments, acid catalyst 408 facilitates the interaction of test sample 302 and test sample 303 with chemical reporters 418 and 420, respectively. Acid catalyst 408 enhances the performance of chemical reporters 418 and 420 (e.g., provided in any order as appropriate), resulting in faster generation of a detectable response at response detectors 424 and 426. For example, acid catalyst 408 may increase the rate of hydrolysis of test sample 302, resulting in a faster response of chemical reporter 418 to nitric acid and faster detection of a response of chemical reporter 418 to nitric acid at response detector 424. Acid catalyst 408 may also facilitate the degradation of test sample 303 to hydrogen peroxide, which can interact with chemical reporter 420 and provide a detectable response at response detector 426.

After interacting with acid catalyst 408, analytes 320 move over each of the chemical reporters 416, 418, and 420. In some embodiments, chemical reporters 416, 418, and 420 may be placed in any order. In addition, although illustrated as discrete sections in FIGS. 4 and 6, chemical reporters 416, 418, and 420 may contact each other and/or may be layered over each other in some embodiments.

In this example, chemical reporter 416 is operable to detect certain military explosives and may be termed a "military explosives chemical reporter." In some embodiments, military explosives chemical reporter 416 includes an amplifying fluorescent polymer or other military chemical reporter. The intensity of light emitted by the amplifying fluorescent polymer varies in response to interaction of the amplifying fluorescent polymer with analytes 320.

For example, the binding of one analyte molecule to the amplifying fluorescent polymer quenches the emission of many polymer repeat units. Thus, when an analyte of interest lands on a polymer binding site, many polymer repeat units in the vicinity of the bound analyte do not emit absorbed light as fluorescence. As a result, the polymer fluorescence is said to be "quenched" by the adsorption of the analyte molecule.

In various embodiments, military explosives chemical reporter 416 is associated with illumination source 412 having an associated wavelength and response detector 422 (e.g., an optical detector). Illumination source 412 (e.g., a LED) emits light 413 in a wavelength that interacts with the amplifying fluorescent polymer to cause the amplifying fluorescent polymer to generate an emission. In certain embodiments, the wavelength is about 400 nm (e.g., 365 nm). In some embodiments, illumination source 412 only illuminates the portion of military explosives chemical reporter 416 that contains the amplifying fluorescent polymer. Response detector 422 (e.g., a photodiode) is positioned to receive the emission generated by the amplifying fluorescent polymer to detect the presence of one or more analytes 320. As shown in FIG. 5, in some embodiments, illumination source 412 and response detector 422 are positioned to be out of line of sight, for example 90 degrees apart. This ensures that light emitted by illumination source 412 is not captured by response detector 422, so that response detector 422 captures mostly the emission generated by the amplifying fluorescent polymer. Other dispositions of illumination source 412 and response detector 422 are contemplated, and illumination source 412 and response detector 422 can be positioned in any desired configuration (e.g., in close proximity or co-located in some embodiments). Inlet 140 is not shown in FIG. 5 for purposes of clarity.

Examples of analytes that are detectable by military explosives chemical reporter 416 are TNT (e.g., test sample 301) and nitroglycerin (e.g., test sample 302). Other substances that may be detected are disclosed in U.S. Pat. No. 6,558,626, which is incorporated by reference in its entirety by express reference thereto.

In an example, chemical reporter 418 is operable to detect certain nitrogen-based explosives, such as nitric acid precursors like nitroglycerin (e.g., test sample 302), and may be termed a "nitric acid chemical reporter." In some embodiments, nitric acid chemical reporter 418 includes a fluorescent compound that is pH sensitive (e.g., acid sensitive). A suitable fluorescent compound is 2-[5-methoxy-2-(4-phenyl-quinoline-2yl)-phenyl]-ethanol, as represented by the following structure:

Other suitable fluorescent compounds are disclosed in U.S. Pat. No. 9,068,960, which is incorporated by reference in its entirety by express reference thereto. Increases or decreases in the response of the fluorescent compound of the nitric acid chemical reporter 418 to light establish the presence of nitric acid (and a nitric acid precursor). For example, upon reaction of nitric acid with the fluorescent compound of the nitric acid chemical reporter 418, the fluorescent compound will undergo a change in fluorescent response intensity.

Nitric acid chemical reporter 418 is associated with illumination source 414 having an associated wavelength (e.g., 365 nm) and response detector 424 (e.g., an optical detector). Illumination source 414 (e.g., a LED) emits light 415 in a wavelength that interacts with the fluorescent compound of the nitric acid chemical reporter 418 to cause the fluorescent compound to generate an emission. Response detector 424 is positioned to receive the emission generated by the fluorescent compound of the nitric acid chemical reporter 418 to detect the presence of nitric acid. Response detector 424 detects the changes in response of the fluorescent compound of the nitric acid chemical reporter 418 to thereby establish the presence of a nitric acid precursor. Illumination source 414 and response detector 424 may be positioned out of line of sight as shown in FIG. 5.

In some embodiments, an initial response baseline may be first established for the fluorescent compound of the nitric acid chemical reporter 418. To establish the baseline response for the fluorescent compound of the nitric acid chemical reporter 418, a user activates illumination source 414 and heaters 120A, 120B, and 120C, allowing each to achieve operational conditions. Then the user presents substrate reporter surface 406 (implemented as a capillary tube in the illustrated embodiments), free of analytes 320, to illumination source 414 and response detector 424 to produce a detectable response from the fluorescent compound of the nitric acid chemical reporter 418. Thus, any response resulting from this process is free of influence from nitric acid, and can be used to detect whether a change in response occurs.

In an example, chemical reporter 420 is operable to detect certain peroxide-based explosives, such as peroxide precursors like TATP (e.g., test sample 303), and may be termed a "peroxide chemical reporter." In some embodiments, peroxide chemical reporter 420 includes a light-emitting peroxide-reactive compound and is associated with response detector 426 (e.g., an optical detector). Light-emitting materials suitable for use may be any luminescent material, including dyes, oligomers, polymers, and combinations thereof. The light-emitting material may be selected to exhibit certain properties, such as a particular emission wavelength, high quantum yield, high output light efficiency when formulated in a peroxide reactive system, and/or compatibility (e.g., solubility) with one or more components of the system. Additional details regarding the light-emitting materials are found in U.S. Pat. No. 9,005,524, which is incorporated by reference in its entirety by express reference thereto.

The light-emitting peroxide-reactive material responds to the hydrogen peroxide generated from peroxide precursors to produce energy in the form of the emission of a photon. In some embodiments, the resulting energy can stimulate luminescence of the light-emitting peroxide-reactive material such that light energy is emitted. The resulting emission may be detected by response detector 426, which signals the presence of hydrogen peroxide (and a peroxide precursor).

Figure 7:
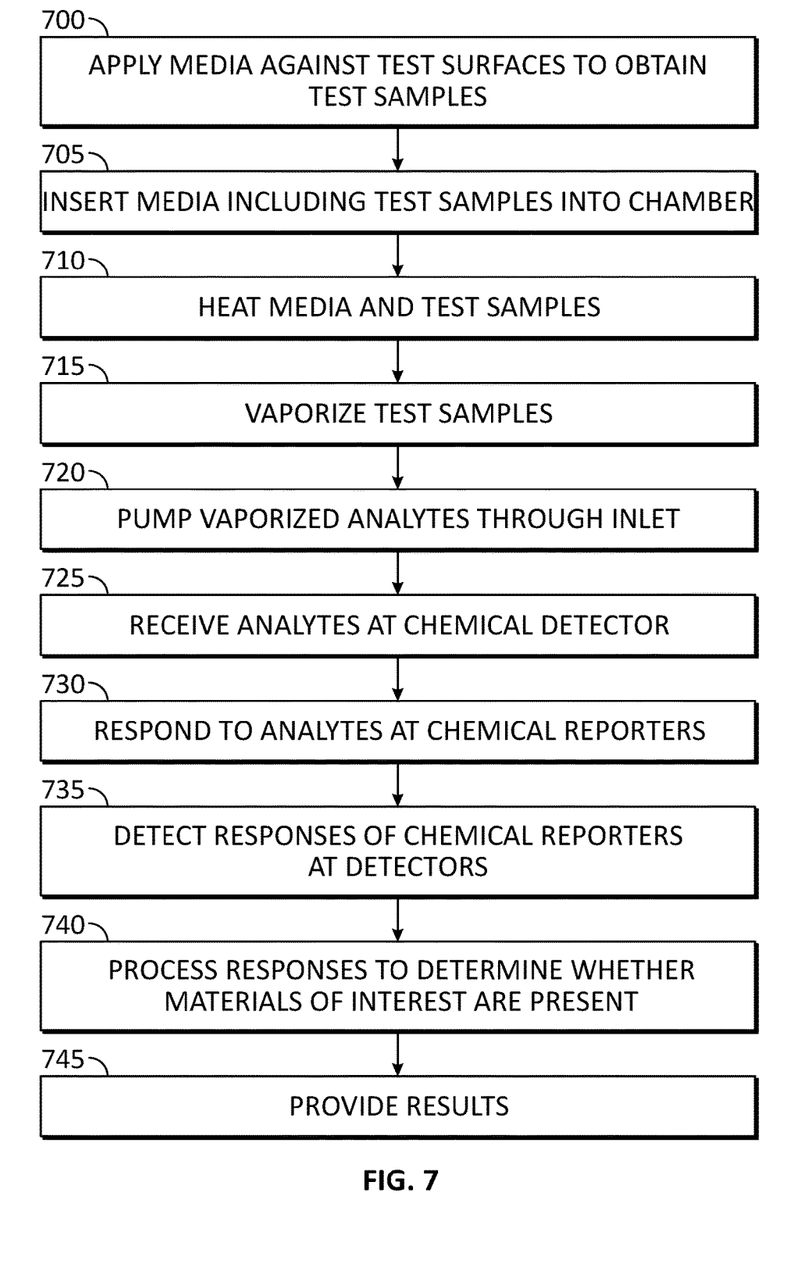
FIG. 7 illustrates a process of operating a trace material detection device in accordance with an embodiment of the disclosure.

FIG. 7 illustrates a process of operating device 100 in accordance with an embodiment of the disclosure. In block 700, a user applies media 300 against a test surface (e.g., a package, luggage, clothing, or other article) to obtain one or more test samples (e.g., test samples 301, 302, and 303 as shown in FIG. 3) corresponding to trace materials residing on the test surfaces.

In block 705, the user inserts media 300 through slot 104 and into chamber 122 as shown in FIG. 3. In block 710, heater 120 applies heat 310 to media 300 and test samples 301, 302, and 303. In various embodiments, processor 112 may operate heater 120 in response to the user's operation of one or more user controls 106 and/or automatically in response to the insertion of media 300 into chamber 122.

In block 715, test samples 301, 302, and 303 are at least partially vaporized to provide analytes 320 in response to heat 310 applied by heater 120. In various embodiments, heat is applied to both sides of media 300, as shown in FIG. 3.

In some embodiments, media 300 and chamber 122 are not required, such as when vapor-phase analytes are directly drawn into inlet 140 from the ambient environment. In such embodiments, blocks 705, 710, and 715 may be omitted and the process of FIG. 7 may begin with block 720.

In block 720, pump 144 operates to draw analytes 320 through inlet 140. In block 725, analytes 320 are received by chemical detector 142 as shown in FIG. 3.

In block 730, chemical reporters respond to the presence of analytes 320. For example, military explosives chemical reporter 416 may respond to the portion of analytes 320 corresponding to test samples 301 and 302, nitric acid chemical reporter 418 may respond to the portion of analytes 320 corresponding to test sample 302, and peroxide chemical reporter 420 may respond to the portion of analytes 320 corresponding to test sample 303.

In block 735, responses of the chemical reporters to the analytes 320 are detected. For example, response detector 422 detects the response of military explosives chemical reporter 416 to the portion of analytes 320 corresponding to test samples 301 and 302, response detector 424 detects the response of nitric acid chemical reporter 418 to the portion of analytes 320 corresponding to test sample 302, and response detector 426 detects the response of peroxide chemical reporter 420 to the portion of analytes 320 corresponding to test sample 303.

In block 740, processor 112 determines whether materials of interest are present based on the responses detected by response detectors 422, 424, and 426. In block 745, the results of block 740 are provided to the user, for example, by messages and/or graphics provided by display 108, audible notifications provided by audio component 132, and/or other techniques as appropriate.

Figure 8:
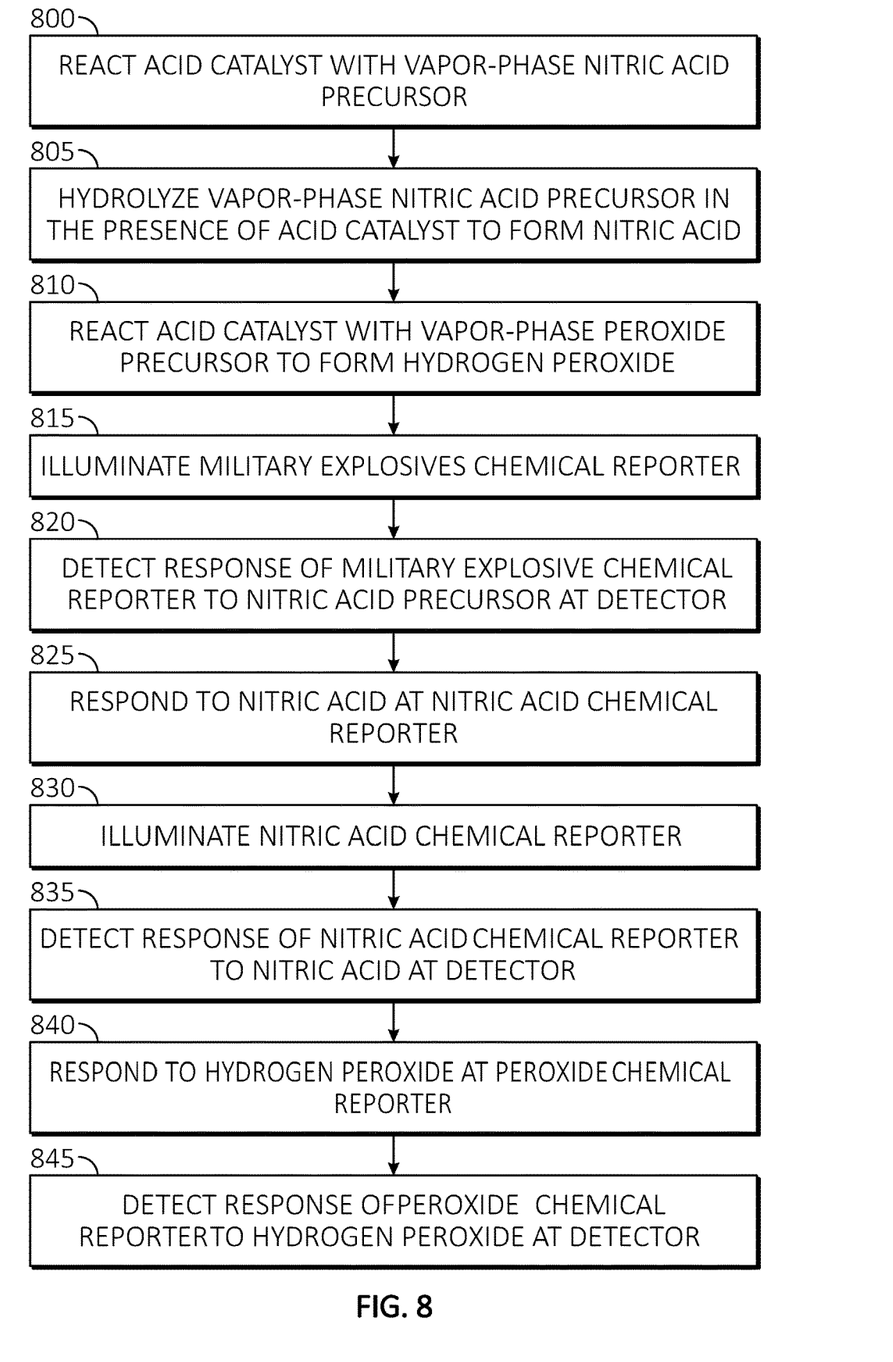
FIG. 8 illustrates a more detailed process of operating a trace material detection device in accordance with an embodiment of the disclosure.

FIG. 8 illustrates more process details performed during one or more of blocks 725-735 of FIG. 7 in embodiments that use emission (e.g., fluorescent and luminescent) techniques. Other detection techniques (e.g., change in resistivity) are contemplated in this disclosure. In block 800, acid catalyst 408 reacts with the portion of analytes 320 including a vapor-phase nitric acid precursor (e.g., corresponding to test sample 302). Referring back to FIG. 4, analytes 320 are drawn into sensing channel 428 by pump 144, and acid catalyst 408 reacts with analytes 320. In block 805, the vapor-phase nitric acid precursor is hydrolyzed in the presence of the acid catalyst 408 to provide nitric acid. In block 810, acid catalyst 408 reacts with the portion of analytes 320 including a vapor-phase peroxide precursor (e.g., corresponding to test sample 303) to form hydrogen peroxide.

In block 815, a military explosives chemical reporter 416 is illuminated. In FIG. 4, military explosives chemical reporter 416 is illuminated by illumination source 412. In block 820, a response of the military explosives chemical reporter 416 to the portion of analytes 320 including the vapor-phase nitric acid precursor is detected at response detector 422. For example, military explosives chemical reporter 416 may respond to the nitric acid precursor to create a change in fluorescent response that is detected by response detector 422. In various embodiments, military explosives chemical reporter 416 may respond to the nitric acid precursor by quenching the military explosives chemical reporter 416.

In block 825, nitric acid chemical reporter 418 responds to the nitric acid produced from the acid catalyzed hydrolysis of the nitric acid precursor. For example, the nitric acid that is formed after exposure of the nitric acid precursor to acid catalyst 408 encounters nitric acid chemical reporter 418. In block 830, the nitric acid chemical reporter 418 is illuminated. As shown in FIG. 4, illumination source 414 illuminates nitric acid chemical reporter 418.

In block 835, a response of the nitric acid chemical reporter 418 to the nitric acid is detected at response detector 424. For example, the interaction between nitric acid and the nitric acid chemical reporter 418 may result in a change in the nitric acid chemical reporter 418 that is detected by response detector 424. In various embodiments, processor 112 determines whether a particular material of interest (e.g., nitric acid precursor) is present in the test sample based on the response of the military explosives chemical reporter 416 and response of the nitric acid chemical reporter 418.

In some embodiments, the change in the nitric acid chemical reporter 418 may be combined with the change in the military explosives chemical reporter 416 to more definitively determine that a nitric acid precursor is present in the test sample. Also, in some embodiments, the relative responses of the nitric acid chemical reporter 418 and the military explosives chemical reporter 416 as received by response detectors 424 and 422 may be compared and analyzed (e.g., by processor 112 in block 740) to identify one or more materials of interest. In this regard, some materials of interest that include nitric acid precursors may cause different relative responses to be exhibited by the nitric acid chemical reporter 418 (e.g., in response to the nitric acid formed by reaction of acid catalyst 408 with the nitric acid precursor) and the military explosives chemical reporter 416 (e.g., in response to the nitric acid precursor analytes themselves responding to the military explosives reporter 416). As such, these different relative responses may permit various materials of interest to be identified with further particularity and accuracy (e.g., through the use of two different chemical reporters 416 and 418).

In block 840, peroxide chemical reporter 420 responds to the hydrogen peroxide produced from the reaction of the peroxide precursor with the acid catalyst 408. In block 845, a response of the peroxide chemical reporter 420 to the hydrogen peroxide is detected at response detector 426. For example, the interaction between the hydrogen peroxide and peroxide chemical reporter 420 may result in a luminescent response of the peroxide chemical reporter 420 that is detected by response detector 426.

Figure 9:
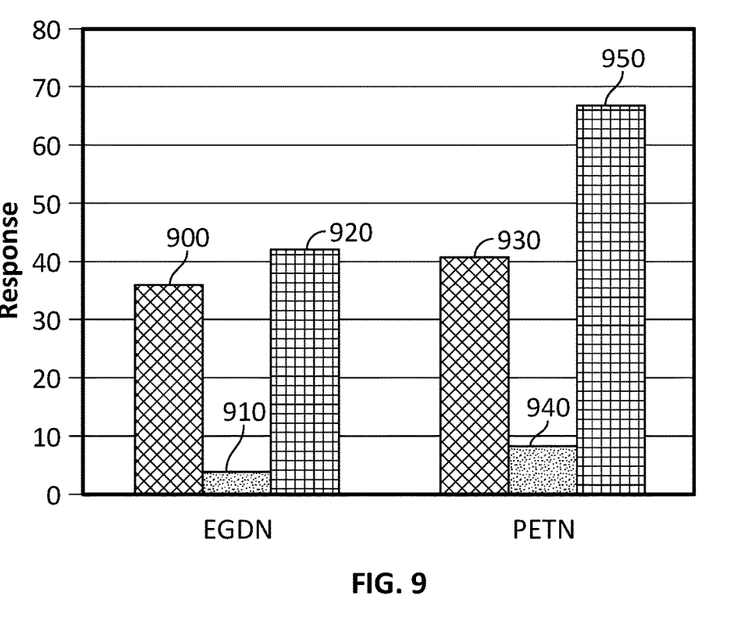
FIG. 9 illustrates a graph comparing various chemical detection techniques in accordance with an embodiment of the disclosure.

FIG. 9 illustrates a graph comparing various chemical detection techniques in accordance with an embodiment of the disclosure. A comparison of the response of nitric acid chemical reporter 418 to EGDN and PETN in the presence of Aquivion® acid catalyst in the form of a strip and a suspension is shown.

Bars 910 and 940 illustrate the response of nitric acid chemical reporter 418 to nitrate esters, for example EGDN and PETN, and to a lesser extent nitramines, for example RDX, when acid catalyst 408 is disposed downstream of nitric acid chemical reporter 418. In other words, acid catalyst does not react with nitrate esters or nitramines before interaction with nitric acid chemical reporter 418.

This results in a relatively low response and low detectability of nitrate esters or nitramines.

In contrast, when acid catalyst 408 is disposed upstream of nitric acid chemical reporter 418 (e.g., as shown in FIGS. 4 and 6), the response of nitric acid chemical reporter 418 to nitrate esters or nitramines is significantly increased as shown in bars 900, 920, 930, and 950. Bars 920 and 950 show an increased detectability with use of Aquivion® acid catalyst in the form of a suspension compared to Aquivion® acid catalyst in the form of a strip (bars 900 and 930).

In view of the present disclosure, it will be appreciated that devices and related methods are provided to detect the presence of trace chemicals corresponding to materials of interest using acid catalyzed hydrolysis. Use of an acid catalyst increases the response of chemical reporters to certain materials of interest, such as nitrogen-based and peroxide-based explosives. Moreover, by using multiple chemical reporters, various materials of interest may be identified with increased accuracy.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

What is claimed is:

1. A device comprising:
an inlet configured to receive a vapor-phase nitric acid precursor;
a solid acid catalyst configured to react with the vapor-phase nitric acid precursor to form nitric acid; and
a chemical detector comprising a chemical reporter configured to respond to the nitric acid, wherein the chemical reporter is configured to detect a response of the chemical reporter to the nitric acid to determine whether materials of interest are present.

2. The device of claim 1, further comprising:
an excitation source having an associated wavelength configured to illuminate the chemical reporter to provide the response as a change in fluorescence in the chemical reporter; and
wherein the chemical detector comprises an optical detector.

3. The device of claim 1, wherein the chemical reporter comprises a colorimetric reporter, a resistive reporter, a luminescent reporter, or an infrared/Raman reporter.

4. The device of claim 1, wherein the detector comprises an optical detector or a resistivity detector.

5. The device of claim 1, wherein the nitric acid precursor comprises one or more of:
a nitrate ester comprising one or more of pentaerythritol tetranitrate (PETN), ethylene glycol dinitrate (EGDN), or nitroglycerin; or
a nitramine comprising cyclotrimethylenetrinitramine (RDX).

6. The device of claim 1, wherein the solid acid catalyst comprises one or more perfluorinated polymers containing sulfonic acid groups.

7. The device of claim 1, wherein the chemical detector comprises a substrate reporter surface having a sensing channel comprising a plurality of chemical reporters disposed therein.

8. The device of claim 6, wherein the solid acid catalyst is disposed within the sensing channel upstream of the plurality of chemical reporters.

9. The device of claim 1, wherein the chemical reporter is a first chemical reporter, and the device further comprises:
a second chemical reporter of the chemical detector configured to receive the vapor-phase nitric acid precursor, wherein the chemical detector is further configured to detect a response of the second chemical reporter to the vapor-phase nitric acid precursor; and
a processor configured to determine whether a particular material of interest is present based on the response of the first chemical reporter and the response of the second chemical reporter.

10. The device of claim 1, wherein:
the chemical reporter is a first chemical reporter;
the inlet is further configured to receive a vapor-phase peroxide precursor;
the solid acid catalyst is further configured to react with the vapor-phase peroxide precursor to form hydrogen peroxide; and
the device further comprises a second chemical reporter of the chemical detector configured to respond to the hydrogen peroxide; and
the chemical detector is further configured to detect a response of the second chemical reporter to the hydrogen peroxide to determine whether materials of interest are present.

11. A method of operating the device of claim 1, comprising:
receiving the vapor-phase nitric acid precursor;
hydrolyzing the vapor-phase nitric acid precursor in the presence of the solid acid catalyst to form nitric acid;
receiving the nitric acid at the chemical reporter; and
detecting, by the chemical detector, a response of the chemical reporter to the nitric acid to determine whether materials of interest are present.

12. The method of claim 11, further comprising:
illuminating the chemical reporter with an excitation source having an associated wavelength to provide the response as a change in fluorescence in the chemical reporter; and
wherein the detecting is performed by an optical detector.

13. The method of claim 11, wherein the chemical reporter comprises a colorimetric reporter, a resistive reporter, a luminescent reporter, or an infrared/Raman reporter.

14. The method of claim 11, wherein the detecting is performed by an optical detector or a resistivity detector of the chemical detector.

15. The method of claim 11, wherein the nitric acid precursor comprises one or more of:
- a nitrate ester comprising one or more of pentaerythritol tetranitrate (PETN), ethylene glycol dinitrate (EGDN), or nitroglycerin; or
- a nitramine comprising cyclotrimethylenetrinitramine (RDX).

16. The method of claim 11, wherein the solid acid catalyst comprises one or more perfluorinated polymers containing sulfonic acid groups.

17. The method of claim 11, wherein the chemical detector comprises a substrate reporter surface having a sensing channel comprising a plurality of chemical reporters disposed therein.

18. The method of claim 17, wherein the solid acid catalyst is disposed within the sensing channel upstream of the plurality of chemical reporters.

19. The method of claim 11, wherein the chemical reporter is a first chemical reporter, and the method further comprises:

receiving the vapor-phase nitric acid precursor at a second chemical reporter of the chemical detector detecting, by the chemical detector, a response of the second chemical reporter to the vapor-phase nitric acid precursor; and determining whether a particular material of interest is present based on the response of the first chemical reporter and the response of the second chemical reporter.

20. The method of claim 11, wherein the chemical reporter is a first chemical reporter, and the method further comprises:

receiving a vapor-phase peroxide precursor:

reacting the solid acid catalyst with the vapor-phase peroxide precursor to form hydrogen peroxide;

receiving the hydrogen peroxide at a second chemical reporter of the chemical detector; and detecting, by the chemical detector, a response of the second chemical reporter to the hydrogen peroxide to determine whether materials of interest are present.

\* \* \* \* \*

UNITED STATES PATENT AND TRADEMARK OFFICE
CERTIFICATE OF CORRECTION

| | | |
|---|---|---|
| PATENT NO. | : 10,209,231 B2 | Page 1 of 1 |
| APPLICATION NO. | : 15/256443 | |
| DATED | : February 19, 2019 | |
| INVENTOR(S) | : Steven Keen, Lara Wald and Mark Fisher | |

It is certified that error appears in the above-identified patent and that said Letters Patent is hereby corrected as shown below:

In the Specification

In the Detailed Description:

In Column 7, Line 44, change "detebtor" to --detector--.

Signed and Sealed this
Seventh Day of May, 2019

Andrei Iancu
*Director of the United States Patent and Trademark Office*